United States Patent [19]
Kauschke et al.

[11] Patent Number: 5,142,898
[45] Date of Patent: Sep. 1, 1992

[54] METHOD FOR OPERATING A MEASURING ARRANGEMENT FOR DETECTING THE COMPONENT OF COMBUSTIBLE GASES IN A GAS MIXTURE

[75] Inventors: Wolfgang Kauschke; Werner Thoren, both of Lübeck, Fed. Rep. of Germany

[73] Assignee: Drägerwerk Aktiengesellschaft, Lübeck, Fed. Rep. of Germany

[21] Appl. No.: 696,088

[22] Filed: May 6, 1991

[30] Foreign Application Priority Data

May 10, 1990 [DE] Fed. Rep. of Germany ....... 4014930

[51] Int. Cl.[5] ............................................. G01N 27/16
[52] U.S. Cl. .................................... 73/23.31; 422/94; 436/137
[58] Field of Search ............... 73/23.31; 436/137; 422/94, 95, 96, 98

[56] References Cited

U.S. PATENT DOCUMENTS

| | | | |
|---|---|---|---|
| 4,305,724 | 12/1981 | Micko | 422/94 |
| 4,475,378 | 10/1984 | Boutonnat et al. | 73/23.31 |
| 4,538,448 | 9/1985 | Boutonnat et al. | |
| 4,817,414 | 4/1989 | Hagen et al. | 73/23.31 |
| 5,055,269 | 10/1991 | Palumbo et al. | 422/96 |
| 5,070,721 | 12/1991 | Tantram | 73/23.31 |

FOREIGN PATENT DOCUMENTS 0018221 10/1980 European Pat. Off. .

Primary Examiner—Hezron E. Williams
Assistant Examiner—Joseph W. Roskos
Attorney, Agent, or Firm—Walter Ottesen

[57] ABSTRACT

The invention is directed to a method of operating a measuring arrangement for detecting combustible gases in a gas mixture with the measuring arrangement including a display unit, a measuring unit, a detector element and a drivable compensator element. The method is improved in that the power input is minimized. This is achieved in that the detector element is supplied with the detector operating current ID during a first operating phase in the operational-ready condition; whereas, the compensator element is driven with a compensator component operating current IK1 and a first measuring signal U1 for gas analysis is formed from the voltages on the detector element and compensator element and that, in a second operating phase, the compensator element is connected in a component heat-up phase to the compensator operating current IK from the switch-in time point t0 to the time point t1 and the steady-state terminal value of the compensator voltages UK(ts) is extrapolated at the end of the heat-up phase from the increase of the compensator voltage UK(t) in the time interval t0 to t1 with a processing function and a second measuring signal U2 for gas analysis is formed with the extrapolated terminal voltage UK(ts) and the voltage UD on the detector element.

19 Claims, 3 Drawing Sheets

$$U_K(t) = U_K(ts) \times [1 - e^{-b(t,T) \times t}] \sim 14$$

METHOD FOR OPERATING A MEASURING ARRANGEMENT FOR DETECTING THE COMPONENT OF COMBUSTIBLE GASES IN A GAS MIXTURE

FIELD OF THE INVENTION

The invention relates to a method for operating a measuring arrangement for detecting the component of combustible gases in a gas mixture. The measuring arrangement includes a display unit, a measuring unit, a detector element and a drivable compensator element.

BACKGROUND OF THE INVENTION

Gas sensors are used for measuring the concentration of combustible gases and they include a catalyzer which is heated to a specific temperature such as 500° C. In this way, the combustible gases are catalytically burned at the sensor surface while consuming a part of the oxygen contained in the gas to be measured.

As a measuring arrangement, it is conventional to utilize an active sensor (detector) and a passive sensor (compensator) in one or two separate measuring bridges. The detector reacts with the gas to be measured; whereas, the compensator functions essentially only for compensating for ambient influences. The compensator is heated to the same temperature as the detector. The measurement voltage below the lower explosion limit is proportional to the concentration of the combustible gas. This measurement voltage is equal to the difference between the detector voltage and the compensator voltage.

A measurement method for measuring the quantity of the components present in a gas and the measuring circuit associated therewith is disclosed in published European patent application 0 018 221 (U.S. patent application Ser. No. 031,750 and filed on Apr. 20, 1979). In the known measuring method, the detector element and the compensator element are arranged in separate measuring bridges and are connected to a common voltage supply. The supply currents are controlled in such a manner that the detector element as well as the compensator element are maintained at preselected temperatures. For this purpose, each bridge is provided with a switching unit in the form of a two-level controller in the voltage supply. This switching unit interrupts the supply current for a time duration when the preselected temperature is exceeded. The calibration of the detector element and compensator element takes place in such a manner that the output voltages are balanced to the same value for a reference gas which is free of combustible components.

For specific applications, the detector element and compensator element operate with voltages of unlike magnitude and therefore at unlike temperatures. The different output voltages are then balanced with a voltage adjusting arrangement at the summing point of the two measuring bridges so that the amplifiers connected downstream thereof see a balanced measuring bridge. This balance takes place again with a reference gas which is free of combustible components.

The known measurement method has the disadvantage that the detector element and compensator element can only operate at fixed predetermined temperatures and the power consumption (especially in the operational-ready phase where no combustible gas is present) is just as great as in the measuring phase with combustible gases. Especially in the case of portable apparatus, large batteries must be taken along to cover the current requirements in order that the power requirement of the measuring apparatus be covered. This makes these apparatus heavy and inconvenient to use.

U.S. Pat. No. 4,538,448 discloses a method for determining the explosion limit of a gas mixture. Here, a detector element is connected to a voltage supply and the supply current is controlled to a constant value after the switch-in time point. The voltage variation at the detector element in dependence upon time is registered by a measuring unit. An extrapolation function is computed from the voltage variation via support values and this extrapolation function is used to determine the explosion limit of the gas mixture.

In the known arrangement, it is disadvantageous that the detector element and also the compensator element are always connected to the operating current during the measuring phase and therefore continuously require the full power input. Furthermore, the system is not ready for measurement during pauses in measurement wherein the detector element is not connected to the supply current.

SUMMARY OF THE INVENTION

It is an object of the invention to provide a continuously operational measurement method for detecting combustible gases which is improved so that the power input is minimized and is adapted to the concentration of the combustible gas to be measured.

The method of the invention is for operating a measuring arrangement for detecting a combustible gas in a gas mixture. The measuring arrangement includes a display unit, a measuring unit connected to the display unit, a detector element, and, a compensator element which can be driven. The method includes the steps of: in a first operating phase, supplying the detector element with a detector operating current ID while supplying the compensator element with a first compensator component operating current IK1 thereby causing a first voltage UD and a second voltage UK to drop across the detector element and the compensator element, respectively; forming a first measuring signal U1 for gas analysis from the first voltage UD and the second voltage UK; in a second operating phase, supplying the compensator element with a second compensator component operating current IK in a partial heat-up phase during a time interval from a switch-in time point t0 to a time point t1; extrapolating the steady-state terminal voltage U(t) at the end of the heat-up phase from the slope of the compensator voltage UK(t) in the time interval t0 to t1 with a processing function; and, forming a second measuring signal U2 for gas analysis from the extrapolated terminal voltage and the first voltage UD.

The primary advantage of the method of the invention is that the compensator element, which compensates for ambient influences, is supplied only with the compensator component operating current IK1 during the first operating phase (the operational-ready phase). The detector element is always connected to the detector operating current ID and is continuously measurement ready and detects the presence of a combustible gas in the measurement gas. A concentration measurement is only possible with limited measurement accuracy because the compensator element is supplied in the first operating phase with the compensator component current IK1. The measurement signal U1 is formed from the voltage drop at the detector element UD and compensator element UK and can be the quotient of both voltages. The measurement signal U1 is evaluated in the measuring unit connected downstream and the determined concentration is displayed.

The concentration is a measure for the combustibility of the gas mixture. If a switch-over criteria stored in the measuring unit is triggered by the measuring signal U1, then the control unit switches the compensator operating current IK to the compensator element in the second operating phase (the so-called measuring phase). This switching action of the control unit is for a predetermined time interval t0 to t1 where t0 is the switch-in time point.

From the voltage variation at the compensator element in the time interval t0 to t1, an extrapolation then takes place to the terminal value of the voltage on the compensator element with the aid of a processing function which would otherwise settle only after a switch-in duration ts of, for example, a half hour. The length of the switch-in duration ts until the steady state terminal value is reached is essentially dependent upon constructive features of the sensor head and the type of compensator utilized. By extrapolating the voltage to the terminal value, the heating operation of the compensator element can be interrupted prematurely and a concentration measurement with a measuring accuracy increased with respect to the first operating phase is possible. The measuring arrangement is continuously ready for measurement notwithstanding the switch-over from the operational phase to the measuring phase. In the second operating phase, the second measuring signal U2 is formed from the extrapolated voltage UK(ts) on the compensator element and the voltage on the detector element UD.

A temperature sensor is provided for detecting the temperature T within the sensor head in the vicinity of the detector element and the compensator element. A platinum resistor (Pt 100, Pt 200) or a semiconductor resistor (KTY) are suitable components since they have an adequate slope of the characteristic line in the relevant temperature range. The temperature signal is applied to the measuring unit and is utilized in the computation of the processing function. The temperature signal compensates for the temperature dependence of the processing function.

The switch-over criteria between the first and second operating phases is preferably such that the switch-over criteria is triggered after a first limit value DU1 is exceeded by the first measuring signal U1. The first limit value DU1 lies in the range of 1% to 20% (preferably 5%) of the lower explosion limit (LEL). This range provides the sensitivity of the switch-over criteria. 5%(LEL) is a significant threshold value above the statistic fluctuations caused by ambient influences for most of the known combustible gases. If the second operating phase has been triggered by exceeding the first limit value DU1 and the gas concentration in the sensor head has remained unchanged during the second operating phase, then the further sequence must be so influenced by the measuring unit that the second operating phase is not subsequently triggered again. This sequence can for example take place such that the first limit value DU1 is raised for a limited time or is again triggered only after a time interval pregiven by the measuring unit.

As an alternative or in combination, it is preferable to initiate the second operating phase after a time t2 pregiven by the measuring unit and to compare the measuring value to the value present in the first operating phase and to check the same as to plausibility. If the deviation lies outside of the stored permissible error bandwidth in the measuring unit, then the compensator element is connected to the compensator operating current IK and is heated to the steady-state terminal voltage UK(ts). A concentration measurement with full measuring accuracy is then possible.

The processing function can be advantageously given as an exponential function of the form:

$$UK(t) = UK(ts) \times [1 - e^{-b(t,T) \times t}]$$

Experiments have shown that the voltage variation at the compensator element can be described as a function of the above-mentioned type wherein UK(t) is the instantaneous voltage at time point t, UK(ts) is the steady-state terminal voltage after the heating time ts and b(t,T) is a factor which is dependent on time t, the gas temperature T and, if required, from ambient influences such as relative humidity of the measuring gas and the composition of the gas. Tests have led to the result that other influence parameters above the switch-in time of the time duration t0 to t1 have no significant effect on the course of the curve of the processing function and therefore on b(t,T) (with the exception of the time t and the ambient temperature T).

The processing function is preferably determined in a separately occurring calibration cycle. For this purpose, the compensator element is connected to the compensator operating current IK and the voltage curve UK(t) at the ambient temperature T is recorded beginning at the switch-in time point t0 at fixed time points and is stored in a permanent memory of the measuring unit. The steady-state terminal value UK(ts) is then the voltage value at the compensator element after the switch-in time ts. The steady-state terminal value is available after approximately 30 minutes according to the compensator type and constructive features of the sensor head.

The dependence of the processing function from the ambient temperature T is determined in that the calibrating cycle is repeated at a second ambient temperature T1. The voltage curve for this temperature is UK1(t). Since the temperature influence is linear, corresponding approximating straight lines can be computed from support values UK(te) and UK1(te) at fixed time te. With these approximating straight lines, compensator voltage values for intermediate temperatures can be determined for each one of fixed times te in the time interval t0 to t1. The calibration curves at the ambient temperatures T and T1 can be recorded as variables characteristic of the sensor head during manufacture and be stored in an EPROM. Later, both components are inserted into the corresponding measuring apparatus at the location of use. Additional calibration curves can be recorded when, for example, a corresponding start signal is triggered manually when taken into service or after a time plan pregiven by the measuring unit or when there is a deviation outside of the permissible error bandwidth between the measured value of the first operating phase and the measured value of the second operating phase. If such a calibrating cycle is for example triggered by a plausibility analysis between first and second operating phases, then, at the gas temperature T2 present, the voltage curve UK2(t) is recorded at fixed time points and is stored in the permanent memory of the measuring unit. With this heating operation, determination of the gas concentration with full measuring accuracy is possible at the end of the heating phase while, on the other hand, an additional calibrating curve for the gas temperature T2 is provided.

In the second operating phase, the compensator element is connected to the compensator operating current IK from the switch-in time point t0 to the time point t1 during a component heating phase. The time interval t0 to t1 amounts to 1 second to 30 seconds and is preferably 10 seconds. Within this time interval at time point te or at the end of the time interval at time point t1, extrapolation to the steady-state terminal value UK(ts) takes place with the processing function. The temperature approximating straight line must be determined for the particular extrapolation time point te or t1 in order to consider the temperature influence.

In the first operating phase, the compensator element is supplied with the compensator component operating current IK1 which amounts to 20% to 80%, preferably 50%, of the compensator operating current IK. At a compensator component operating current of 50%, extrapolation to the steady-state terminal value UK (ts) can take place already after a few seconds of heating time with good accuracy. This value constitutes an optimum between power savings in the first operating phase and a rapid measuring readiness in the second operating phase.

It is preferable during a third operating phase to supply the compensator element continuously with the compensator operating current IK for increased components of combustible gases in the gas mixture or when there are large changes in concentrations. The third operating phase can be triggered after exceeding a second limit value DU2 of the second measuring signal U2 which can amount to 40% to 140% (lower explosion limit) and preferably 40% (lower explosion limit). The third operating phase can also be triggered after a fixed time t3 pregiven by the measuring unit.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
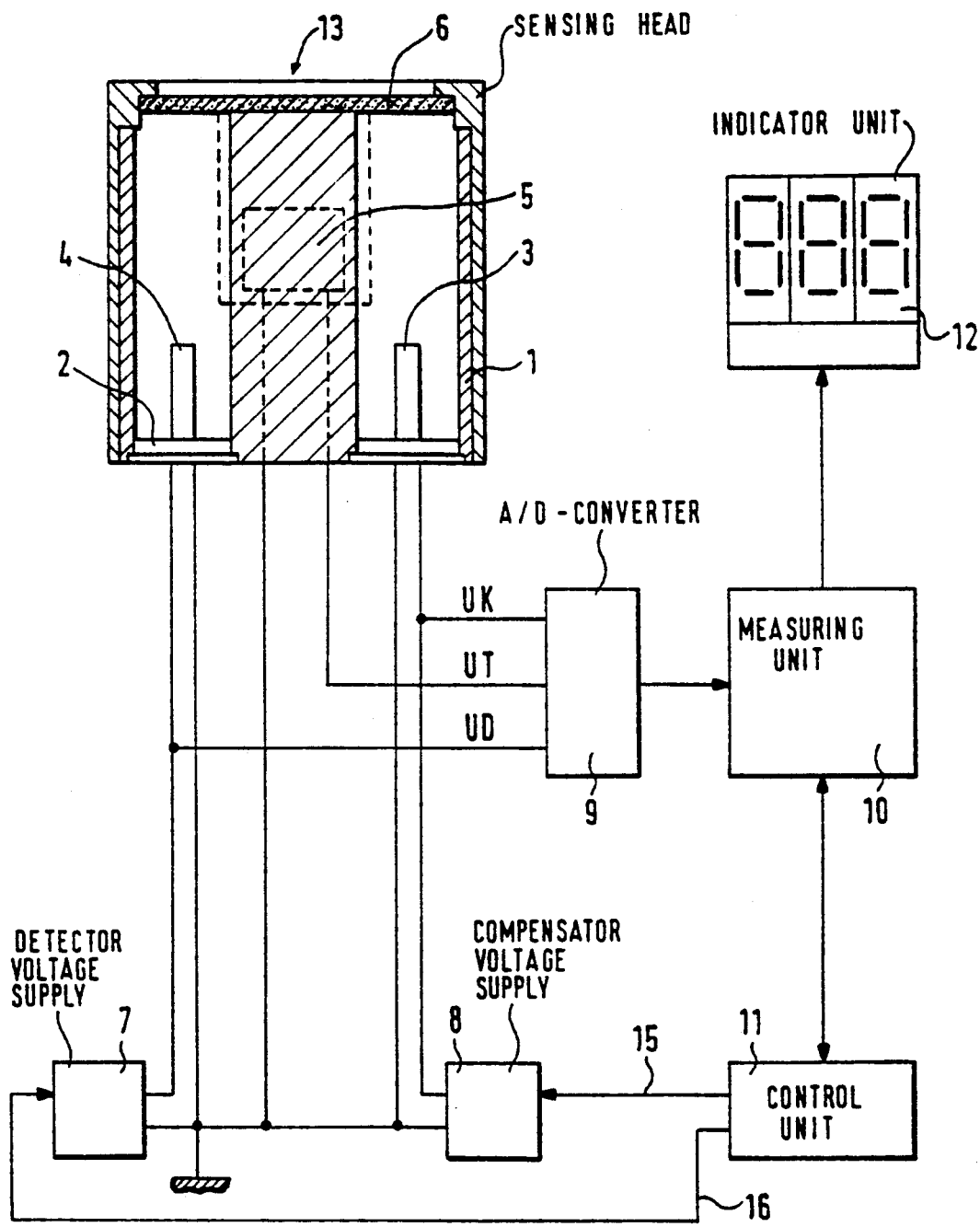
FIG. 1 is a circuit block diagram of the measuring arrangement for carrying out the method of the invention.

The measuring arrangement shown in FIG. 1 includes the following: a sensor head 13, a detector voltage supply 7, a compensator voltage supply 8, an analog-to-digital converter 9, a measuring unit 10, a display or indicator unit 12 and a control unit 11. A detector element 4 and a compensator element 3 are mounted on a supporting plate 2 in the sensor head 13. The gas to be measured penetrates into the sensor head 13 via a sintered metal disc 6 and is catalytically burned on the detector element 4. The measurement gas temperature within the sensor head 13 is measured with a platinum resistor which functions as a temperature sensor 5. The measurement signals UD, UK and UT from the detector element 4, compensator element 3 and temperature sensor 5, respectively, are converted in the analog-to-digital converter 9 into digital signals and supplied to the measuring unit 10. The control unit 11 is connected to the measuring unit 10 as well as to the voltage supplies (7, 8) and supplies current control pulses via signal lines (15, 16) for the detector element 4 and the compensator element 3. The measuring unit 10 includes essentially a microprocessor and a permanent memory for storing processing functions and a computer unit for computing voltage values for the extrapolation of the compensator voltage and for converting the measured voltages on the compensator element 3 and the detector element 4 into gas concentration values.

Figures 2, 3:
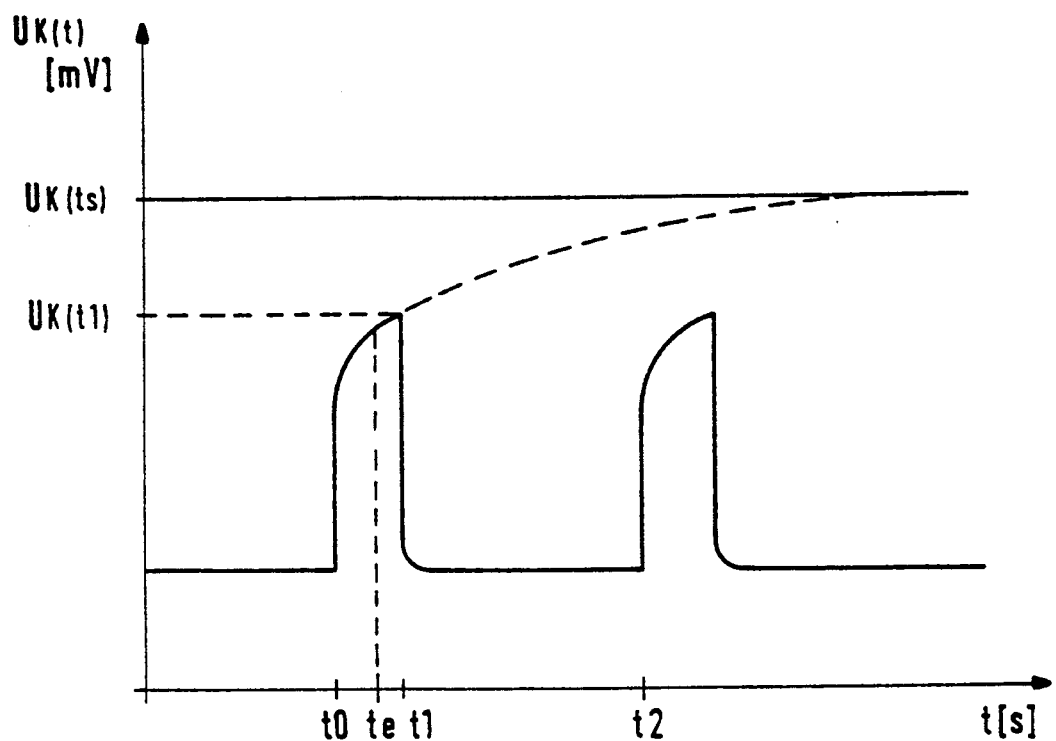
FIG. 2 is a waveform showing the variation of the voltage at the compensator element during clocked pulse operation.
FIG. 3 shows the processing function for computing the compensator terminal voltage.

FIG. 2 shows the voltage variation UK(t) on the compensator element 3 in dependence upon time t in a change-over from the first operating phase to the second operating phase. First, the compensator element 3 is supplied with a compensator component operating current IK1 in the first operating phase. The time point t0 marks the start of the second operating phase and at this time point, the compensator operating current IK is connected. The solid line in FIG. 2 shows the voltage variation UK(t) on the compensator element 3. At time point t1, the second operating phase is completed and the current IK1 is again applied to the compensator element. The broken-line curve above the time t1 shows the voltage variation UK(t) qualitatively if the compensator element 3 would be heated beyond the time point t1 to the steady-state terminal value UK(ts). The steady-state terminal value is here reached after approximately 30 minutes. The time ts cannot be illustrated in the selected scale since it amounts to approximately 30 minutes whereas, t1 is only 10 seconds. At time point t2, a new heating phase is initiated. In the illustrated embodiment, t1 is approximately 10 seconds and t2 approximately 30 seconds referred to the switch-in time point t0.

FIG. 3 shows the processing function 14 for extrapolating the compensator voltage to the steady-state terminal value after the time ts. Experiments have shown that the voltage variation at the compensator element 3 can be described by an exponential function of the above-mentioned form wherein: UK(t) is the instantaneous voltage at the time point t; UK(ts) is the steady-state terminal voltage after the heating time ts; and, b(t,T) is a factor which is dependent upon the time t, the gas temperature T and the ambient influences such as the relative humidity of the measurement gas and the composition of the gas.

Figure 4:
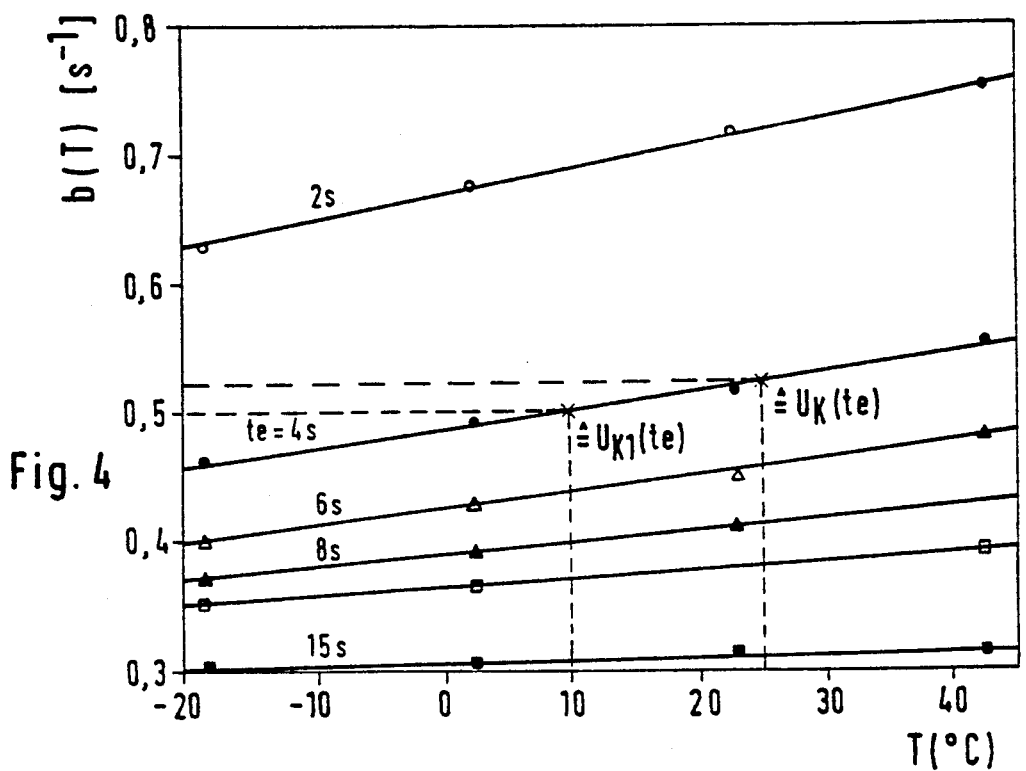
FIG. 4 is a graph showing the factor b(t,T) plotted as a function of temperature T; and, FIG. 5 is a graph showing the voltage difference between measured voltage and extrapolated compensator terminal voltage as a function of time after the time ts of 30 minutes.

FIG. 4 shows the variation of b(t,T) as a function of ambient temperature T. The heat-up time t is shown as a curve parameter where te is a fixed time point within the heat-up time. Because of the linear relationship of b(T) with the temperature T, the temperature dependence can be approximated with a straight line if at least two support values are present for a corresponding heat-up time te. These support values are determined in that the compensator element is connected to the compensator operating current IK in a calibrating cycle with two different ambient temperatures T and T1 and the voltages UK(t) from the first calibrating cycle and UK1(t) from the second calibrating cycle are recorded at the compensator element 3 at fixed time intervals starting at the start point t0 up to the steady-state terminal value ts and stored in the permanent memory of the measuring unit 10.

The support values for the temperature approximating line are then the voltage values of UK(te) and UK1(te) at the ambient temperatures T and T1 referred to the same time te on the particular switch-in point t0. In this way, for each ambient temperature T, an extrapolation function is available in the measuring unit 10 from time point te to the steady-state terminal value at time point ts. te is a pregiven time point for the extrapolation within the interval t0 to t1. The extrapolation is of greater accuracy the greater that the time te is selected; that is, the closer te lies to t1.

Figure 5:
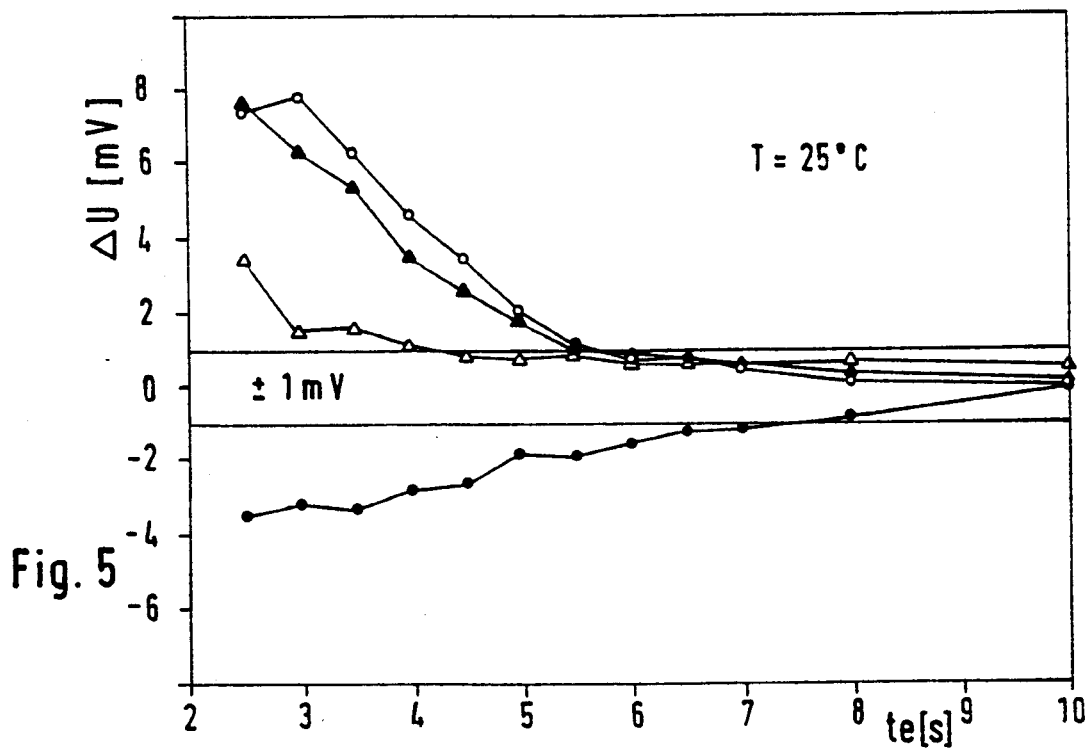

The quality of the extrapolation of the processing function 14 in dependence upon the time te is shown in FIG. 5. Here, different ambient conditions were considered such as the relative humidity of the gas of, for example, 50% relative humidity and 75% relative humidity and gas concentrations c($CH_4$) of 2 Vol % and c($H_2$) of 1 Vol % at constant ambient temperature T of 25° C. For each ambient condition, the real heat-up curve UK(t) is measured and from all curves, always at the same time te, the b(te,T) values are determined and averaged for the time point te. The steady-state terminal value UK(ts) is extrapolated with the processing function 14 from different time points te with averaged b(te,T)-values and the extrapolated value is compared with the measured value. The voltage difference $\Delta U$ is indicated along the ordinate. The range of $\pm 1$ mV is a fixed error limit for the precision of the extrapolation.

FIG. 5 shows that the ambient influences fall off after a certain time and no longer have a significant influence on the extrapolation. In the illustrated embodiment, the extrapolated terminal value UK(ts) lies within the selected error boundary for times te greater than 7 seconds. The extrapolation is possible at each time point within the time interval t0 to t1; however, the precision is greater the closer te lies to t1.

A typical measuring sequence will now be described.

First, a calibration cycle is triggered in that the compensator element 3 is connected to the compensator operating current IK at two different ambient temperatures T and T1. At fixed time intervals (for example, from start point t0 every 0.1 seconds and after 20 seconds, every 5 seconds), the voltage value UK(t) is measured at the compensator element 3 at a temperature T and the voltage value UK1(t) is measured there at temperature T1 and stored in a permanent memory of the measuring unit 10. Voltage values at intermediate temperatures are determined by the measuring unit from both calibrating curves by linear extrapolation with support values being utilized from both curves at the same time te. The calibration curves can also be recorded during the manufacture of the sensor head 13 and stored in an EPROM with both components then being later inserted into the measuring apparatus.

The measuring phase begins with the first operating phase (the operational-ready phase) wherein the detector element 4 is connected to the detector operating current ID; whereas, the compensator element 3 is supplied with the compensator component operating current IK1. For example, ID=100 mA and IK1=50 mA. The measurement signal for the corresponding gas concentration can be U1. If the concentration of a combustible gas increases in the measuring gas (for example $CH_4$ in air), the measuring signal U1 reaches a first limit value DU1 and a second operating phase is initiated. Here, the measuring unit 10 switches the full compensator operating current IK to the compensator element for the time duration t0 to t1 and heats up the compensator element. At the same time, the ambient temperature in the sensor head 13 is measured with the temperature sensor 5. At time point te, extrapolation takes place to the steady-state terminal value of the compensator voltage UK(ts) with the calibrating curves stored in the permanent memory of the measuring unit 10. Already at time point te, a measurement can be made as though the compensator element 3 had been heated to the steady-state terminal value. If the second operating phase has been triggered by exceeding the first limit value DU1 and the gas concentration in the sensor head during the second operating phase has remained unchanged, then the further sequence must be so influenced by the measuring unit 10 that the second operating phase is not again triggered thereafter. This sequence can, for example, take place such that the first limit value DU1 is raised for a limited time or can only again be triggered after an interval pregiven by the measuring unit 10. The change-over between the first and second operating phases can also take place at fixed times pregiven by the measuring unit 10 in that, alternatingly, after for example 20 seconds operational-ready phase, a measuring phase of 10 seconds follows. The advantage here is that for continuous measuring operational readiness of 30 seconds, the full power is needed only for 10 seconds.

A switch-over into the third operating phase takes place for increased concentrations of combustible gases or for rapidly changing gas concentrations. In this third operating phase, the detector element 4 and the compensator element 3 are continuously supplied with operating currents ID and IK, respectively. This operating phase can also be switched in by the measuring unit 10 at fixed time points such as every hour in order to obtain reference measuring values having complete measuring accuracy which also permit conclusions to be made as to possible sources of error in the measuring system. An error recognition is also then possible in the change-over from the first and second operating phases in that the individual measuring signals U1 of the second operating phase are correlated with each other and are checked for plausibility. Furthermore, the possibility is provided that within the second operating phase, several extrapolations at different time points te can be carried out and these extrapolated values are correlated with each other. In this way, random fluctuations can be reduced.

It is understood that the foregoing description is that of the preferred embodiments of the invention and that various changes and modifications may be made thereto without departing from the spirit and scope of the invention as defined in the appended claims.

What is claimed is:

1. A method for operating a measuring arrangement for detecting a combustible gas in a gas mixture, the measuring arrangement including a display unit, a measuring unit connected to the display unit, a detector element, and, a compensator element which can be driven, the method comprising the steps of:

in a first operating phase, supplying the detector element with a detector operating current ID while supplying the compensator element with a first compensator component operating current IK1 thereby causing a first voltage UD and a second voltage UK to drop across said detector element and said compensator element, respectively;

forming a first measuring signal U1 for gas analysis from said first voltage UD and said second voltage UK;

in a second operating phase, supplying the compensator element with a second compensator component operating current IK in a partial heat-up phase during a time interval from a switch-in time point t0 to a time point t1;

extrapolating the steady-state terminal voltage U(t) at the end of the heat-up phase from the slope of the compensator voltage UK(t) in the time interval t0 to t1 with a processing function; and, forming a second measuring signal U2 for gas analysis from the extrapolated terminal voltage and said first voltage UD.

2. The method of claim 1, the measuring arrangement including: a sensor head for accommodating said detector element and said compensator element therein; and, the method wherein the temperature T is detected at said detector element and said compensator element with a temperature sensor arranged in said sensor head.

3. The method of claim 1, wherein said second operating phase is triggered after said first measuring signal exceeds a first limit value DU1 of said first measuring signal U1.

4. The method of claim 3, wherein said first limit value DU1 lies in a range of 1% to 20% of the lower explosion limit (LEL).

5. The method of claim 4, said first limit value DU1 being 5% of the lower explosion limit (LEL).

6. The method of claim 1, wherein said second operating phase is triggered after a time t2 pregiven by said measuring unit.

7. The method of claim 1, wherein said processing function is an exponential function of the form:

$$UK(t) = UK(ts) \times [1 - e^{-b(t,T) \times t}]$$

wherein: b(t,T) is a factor dependent on temperature and time, said factor being dependent upon ambient influences.

8. The method of claim 7, comprising the further steps of: determining said processing function in a separately occurring calibration cycle by heating said compensator element to the steady-state terminal temperature with said compensator operating current IK in preselected time segments, recording the voltage curve UK(t) at constant temperature T; and, storing said voltage curve UK(t) in a permanent memory of the measuring unit.

9. The method of claim 8, to determine the temperature influence of b(t,T), the method comprises the further steps of: recording a second voltage curve UK(t) at a second ambient temperature T1; and, computing the particular temperature approximating straight line from support values UK(te) and UK1(te) at fixed time te.

10. The method of claim 8, when said calibrating cycle is automatically triggered by said measuring unit.

11. The method of claim 1, wherein said time interval t0 to t1 in said second operating phase has a duration of 1 to 30 seconds.

12. The method of claim 11, wherein said duration is 10 seconds.

13. The method of claim 1, wherein said compensator component operating current IK1 is 20 to 80% of said compensator operating current IK.

14. The method of claim 13 wherein said compensator component operating current IK1 is 50% of said compensator operating current IK.

15. The method of claim 1, wherein said compensator element is driven continuously with said compensator operating current during a third operating phase.

16. The method of claim 15, wherein said third operating phase is triggered when a second limit value DU2 of said second measuring signal U2 is exceeded.

17. The method of claim 16, wherein said second limit value DU2 is 40% to 140% (LEL).

18. The method of claim 17, wherein said second limit value DU2 is 40% (LEL).

19. The method of claim 15, wherein said third operating phase is triggered after a time t3 by said measuring unit.

* * * * *